United States Patent [19]

Mase et al.

[11] Patent Number: 4,505,802
[45] Date of Patent: * Mar. 19, 1985

[54] OXYGEN CONCENTRATION DETECTOR

[75] Inventors: Syunzo Mase, Ama; Shigeo Soejima, Nagoya, both of Japan

[73] Assignee: NGK Insulators, Ltd., Japan

[*] Notice: The portion of the term of this patent subsequent to Oct. 4, 2000 has been disclaimed.

[21] Appl. No.: 380,283

[22] Filed: May 20, 1982

[30] Foreign Application Priority Data

May 25, 1981 [JP] Japan .................. 56-77922

[51] Int. Cl.³ ........................... G01N 27/46
[52] U.S. Cl. ................... 204/425; 204/412; 204/426; 204/427; 219/505; 219/553
[58] Field of Search .......... 204/1 S, 421–429; 422/98; 219/505, 553

[56] References Cited

U.S. PATENT DOCUMENTS

| | | | |
|---|---|---|---|
| 3,924,098 | 12/1975 | Dunn | 219/553 |
| 4,101,454 | 7/1978 | Kulwicki et al. | 219/553 |
| 4,107,019 | 8/1978 | Takao et al. | 204/425 |
| 4,145,272 | 3/1979 | Nakamura . | |
| 4,167,163 | 9/1979 | Moder | 204/424 |
| 4,265,724 | 5/1981 | Haecker . | |
| 4,293,838 | 10/1981 | Wahlers et al. | 219/553 |
| 4,321,577 | 3/1982 | Carlson | 422/98 |
| 4,407,704 | 10/1983 | Mase et al. | 204/425 |

FOREIGN PATENT DOCUMENTS

| | | | |
|---|---|---|---|
| 0030164 | 6/1981 | European Pat. Off. | 204/427 |
| 0079246 | 6/1981 | Japan | 204/428 |

Primary Examiner—T. Tung
Attorney, Agent, or Firm—Parkhurst & Oliff

[57] ABSTRACT

An oxygen concentration detector comprises an oxygen ion conductive solid electrolyte and electrodes provided thereon to form an oxygen concentration cell for detecting oxygen partial pressure in a gas such as exhaust gas from an internal combustion engine. The oxygen concentration detector according to the invention further comprises an AC power source supplying to the electrodes an AC having a frequency at which a polarization of AC component is caused mainly due to a polarization of the solid electrolyte to detect an impedance of the solid electrolyte and the electromotive force of the oxygen concentration cell.

11 Claims, 19 Drawing Figures

FIG._1
*PRIOR ART*
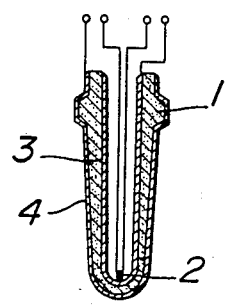
FIG._2
*PRIOR ART*
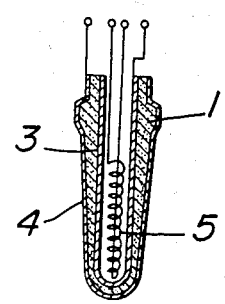
FIG._3
*PRIOR ART*
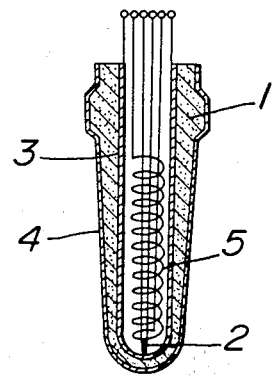

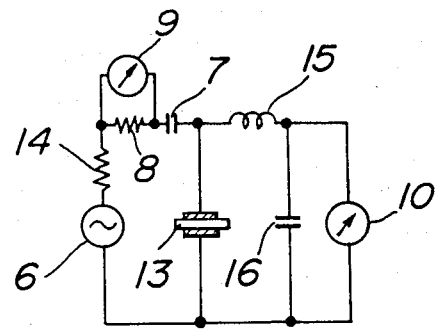
FIG_15
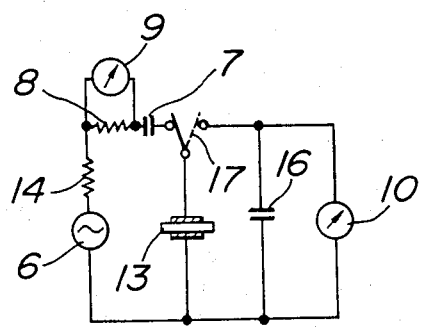
FIG_16

OXYGEN CONCENTRATION DETECTOR

BACKGROUND OF THE INVENTION

1. Field of the Invention

The present invention relates to an oxygen concentration detector which can accurately and rapidly detect particularly an oxygen concentration in a low temperature gas.

2. Description of the Prior Art

Heretofore, the oxygen concentration detector which determines an oxygen concentration in combustion gas exhausted from an internal combustion engine based on the principle of an oxygen concentration cell by using oxygen ion conductive solid electrolyte, has been widely known. For example, the oxygen concentration detector using zirconia ceramics added with yttria as a solid electrolyte and platinum as electrodes has been mainly practically used. This oxygen concentration sensing device is used for detecting a point where an air-fuel ratio λ of the internal combustion engine is 1.0 but in order to detect the point where λ is not 1.0 based on Nernst equation, it is necessary not only to accurately determine an electromotive force of the oxygen concentration cell but also to accurately determine the temperature. For the purpose, for example, it has been proposed that as shown in FIG. 1, a temperature detecting element 2 is inserted and disposed in a cylinder of a tubular solid electrolyte 1, one end of which is closed and which is provided with electrodes 3 and 4 on the inner and external surfaces and the temperature of the solid electrolyte 1 is determined. However, the temperature of the solid electrolyte when being exposed to the exhaust gas, is not uniform throughout the whole but causes unevenness owing to the flow rate of the exhaust gas, so that it is impossible to show the whole solid electrolyte by the measurement at only one point. Furthermore, when the exhaust gas temperature is varied, a time delay occurs and it is very difficult to accurately determine the temperature of the solid electrolyte and the structure becomes complicated.

In such an oxygen concentration detector, at a low temperature, the catalytic activity of platinum and the like lowers and the electric resistance of the solid electrolyte itself become high and the impedance as the oxygen detector becomes higher, the influence of noise is high and the response is slow, so that the lower limit of the practically used temperature is about 350° C. However, the temperature of the exhaust gas of the internal combustion engine may be lower than said lower limit when starting or driving at a low speed and it is impossible to fully develop the function. For obviating this defect, it has been proposed to insert a coil-formed heating wire 5 in a cylinder of the solid electrolyte 1 as shown in FIG. 2 to heat the solid electrolyte 1 but in this case the structure becomes complicated and the electric power as high as several tens watts is required. In addition, it has been proposed that as shown in FIG. 3, a temperature detecting element 2 and a coil-formed heating wire 5 are inserted in a cylinder of the solid electrolyte 1 to heat the solid electrolyte 1 and concurrently detect the temperature but the structure in this case becomes more complicated and this device is poor in the practicability.

SUMMARY OF THE INVENTION

An object of the present invention is to provide an oxygen concentration detector which can obviate these prior defects and stably detect the temperature of the solid electrolyte even in the use for a long period of time and rapidly detect the temperature variation of the solid electrolyte due to variation of the exhaust gas temperature and further can effect the stable heating.

An object of the present invention is to provide an oxygen concentration detector for detecting the oxygen concentration in gases comprising, an oxygen ion conductive solid electrolyte body, at least two separate electrodes contacting the solid electrolyte body so as to form an oxygen concentration cell for detecting oxygen partial pressure in a gas, electromotive force detecting means connected to said electrodes for detecting an electromotive force of the oxygen concentration cell, AC supply means connected to said electrodes for applying an AC voltage to said solid electrolyte through said electrodes, impedance detecting means connected to said electrodes for detecting an impedance of said solid electrolyte, said AC supply means being operable at AC frequencies which are not lower than a frequency whose complex impedance characteristics which when graphed in the manner shown in FIG. 5 hereof, correspond to points B of said graphed complex impedance characteristics.

Another object of the present invention is to provide an oxygen concentration detector for detecting the oxygen concentration in gases comprising, an oxygen ion conductive solid electrolyte body, at least two separate electrodes contacting the solid electrolyte body so as to form an oxygen concentration cell for detecting oxygen partial pressure in a gas, electromotive force detecting means connected to said electrodes for detecting an electromotive force of the oxygen concentration cell, at least one another electrode contacting the solid electrolyte body, AC supply means connected to at least said another electrode for applying an AC voltage to said solid electrolyte, impedance detecting means connected to at least said another electrode for detecting an impedance of said solid electrolyte, said AC supply means being operable at AC frequencies which are not lower than a frequency whose complex impedance characteristics, which when graphed in the manner shown in FIG. 5 hereof, correspond to point B of said graphed complex impedance characteristics.

A further object of the present invention is to provide the detector, wherein the AC has a frequency such that its complex impedance characteristics, when graphed in the manner of FIG. 5 hereof, correspond to point C of said graphed complex impedance characteristics.

A still further object of the present invention is to provide an oxygen concentration detector for detecting the oxygen concentration in gases comprising, an oxygen ion conductive solid electrolyte body, at least two separate electrodes contacting the solid electrolyte body so as to form an oxygen concentration cell for detecting oxygen partial pressure in a gas, electromotive force detecting means connected to said electrodes for detecting an electromotive force of the oxygen concentration cell, AC supply means connected to said electrodes for applying an AC voltage to said solid electrolyte through said electrodes, impedance detecting means connected to said electrodes for detecting an impedance of said solid electrolyte, said AC supply means being operable at AC frequencies which are not lower than a frequency whose complex impedance characteristics, which when graphed in the manner shown in FIG. 5 hereof, correspond to point B of said graphed complex impedance characteristics, wherein said solid electrolyte is self-heated to a high temperature by applying the AC voltage.

Another object of the present invention is to provide an oxygen concentration detector for detecting the oxygen concentration in gases comprising, an oxygen ion conductive solid electrolyte body, at least two separate electrodes contacting the solid electrolyte body so as to form an oxygen concentration cell for detecting oxygen partial pressure in a gas, electromotive force detecting means connected to said electrodes for detecting an electromotive force of the oxygen concentration cell, at least one another electrode contacting the solid electrolyte body, AC supply means connected at least said another electrodes for applying an AC voltage to said solid electrolyte, impedance detecting means connected to at least said another electrodes for detecting an impedance of said solid electrolyte, said AC supply means being operable at AC frequencies which are not lower than a frequency whose complex impedance characteristics, which when graphed in the manner shown in FIG. 5 hereof, correspond to point B of said graphed complex impedance characteristics, wherein said solid electrolyte is self-heated to a high temperature by applying the AC voltage.

Another object of the present invention is to provide wherein the AC current and the AC voltage between the electrodes have a negative relation.

Another object of the present invention is to provide the detector, wherein the AC has a frequency such that its complex impedance characteristics, when graphed in the manner of FIG. 5 hereof, correspond to point C of said graphed complex impedance characteristics.

BRIEF DESCRIPTION OF THE DRAWINGS

FIG. 1–FIG. 3 are schematic views showing cross-section of essential portions of prior oxygen concentration detector;

FIG. 15 and FIG. 16 are schematic views showing the embodiments of circuit for applying AC voltage and detecting the electromotive force in the oxygen concentration detector of the present invention;

DETAILED DESCRIPTION OF THE PREFERRED EMBODIMENTS

In order that the invention may be more clearly understood, preferred embodiments will be described, by way of example, with reference to the accompanying drawings. The alternating current (AC) to be applied in this case is preferred to be one having a frequency at which a polarization of the AC current is caused mainly due to a bulk resistance $R_3$ of crystal grain of the solid electrolyte. More preferably, the present invention lies in an oxygen concentration detector which detects the impedance of the solid electrolyte and detects the electromotive force under the state where the solid electrolyte is self-heated to a high temperature by applying the AC voltage. The AC current passed in this case is preferred to be an electric current of a zone where the AC voltage between the AC current and the electrodes shows the negative relation and/or an AC current having a frequency at which the impedance of an electrostatic capacitance $C_2$ of grain boundary of the solid electrolyte is smaller than the resistance $R_2$ of the grain boundary of the solid electrolyte or an AC current having a frequency at which the polarization of an AC current is caused mainly due to the bulk resistance $R_3$ of the crystal grains of the solid electrolyte.

Since the oxygen concentration detector which determines the oxygen concentration in the exhaust gas of the internal combustion engine and the like, is required to endure a high temperature and to show a rapid response even at a low temperature, for the electrode at the side positioning the gas to be determined, the metals having a higher catalytic activity and a higher melting point, for example, platinum group of metals are used.

Figure 4A:
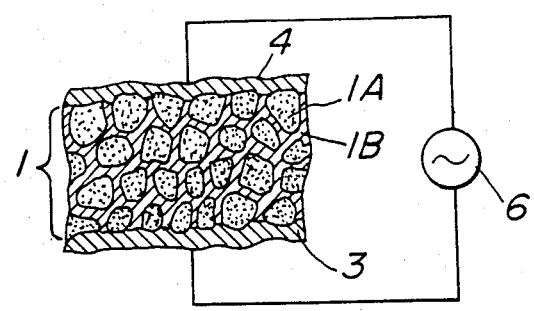
FIG. 4A is a schematic view showing cross-section of essential portions of oxygen concentration detector according to the present invention.

FIG. 4A illustrates one embodiment diagrammatically showing cross-section of the essential portion of the oxygen concentration detector according to the present invention.

Preferring to FIG. 4A, reference numeral 1 is an oxygen ion conductive solid electrolyte body, and said solid electrolyte body 1 comprises a plurality of fine grain 1A having a negative temperature coefficient of electric resistance and highly resistant region layers 1B interposed between the fine grains. Reference numeral 3, 4 are electrodes attached on both side of said solid electrolyte body 1, 6 is AC power source for applying AC current through said solid electrolyte, said electrodes 3, 4 consist of gold, platinum or the like.

Figure 4B:
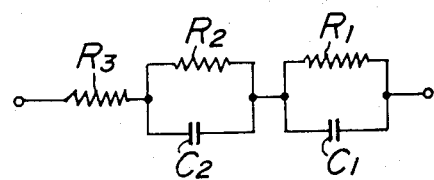
FIG. 4B is a diagram showing an equivalent circuit of the oxygen concentration cell.

The equivalent circuit of the impedance of this oxygen concentration cell is shown in FIG. 4B. Referring FIG. 4B, $R_1$ is a polarization resistance at the interface between the electrode 3,4 and the solid electrolyte 1, $C_1$ is an electric capacitance due to the polarization of the interface between the electrode 3, 4 and the solid electrolyte 1, $R_2$ is a resistance of the grain boundary 1B of the solid electrolyte 1, $C_2$ is an electrostatic capacitance of the grain boundary 1B of the solid electrolyte 1 and $R_3$ is a resistance of the grains 1A of the solid electrolyte 1.

Figure 5:
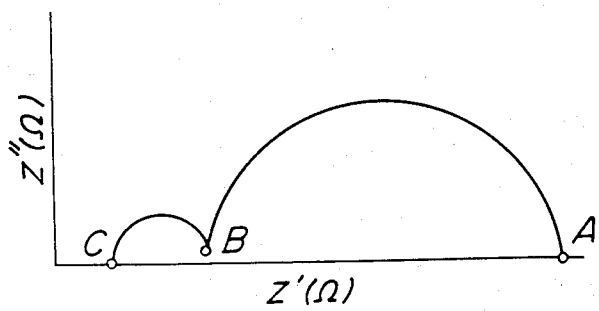
FIG. 5 is a graph showing the complex impedance characteristics of an oxygen concentration cell.

The frequency characteristics of the impedance of the oxygen concentration cell shown by such equivalent circuit are shown by two continuous semi-circular arcs as shown in FIG. 5 in the expression of a complex impedance $Z=Z'-JZ''$, the resistance value of a point A corresponds to the sum of the three resistances $R_1+R_2+R_3$ in FIG. 4B, the resistance value of the point B corresponds to the sum of $R_2+R_3$, and the resistance value of the point C corresponds to the resistance $R_3$. The polarization of the oxygen concentration cell from the point A to the point B on the characteristics curve is mainly due to the resistance $R_1$ and the capacitance $C_1$, and that from the point B to the point C is mainly due to the resistances $R_2$, $R_3$ and the capacitance $C_2$. With respect to the relation of the points A, B and C to the frequency, the impedance at the point A is obtained for DC and as the frequency increases, the complex impedance varies along the arcuate locus toward the point B and further along the other arcuate locus toward the point C.

Figure 6:
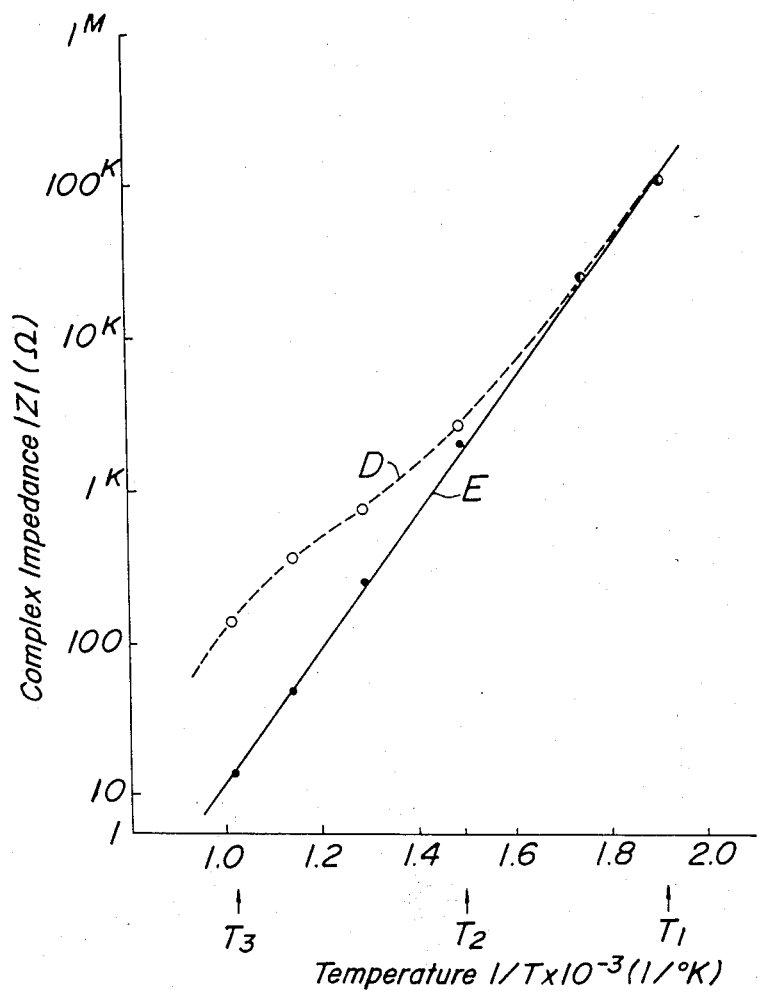
FIG. 6 is a graph showing the relation of the impedance of the oxygen concentration cell to the temperature.
Figure 7:
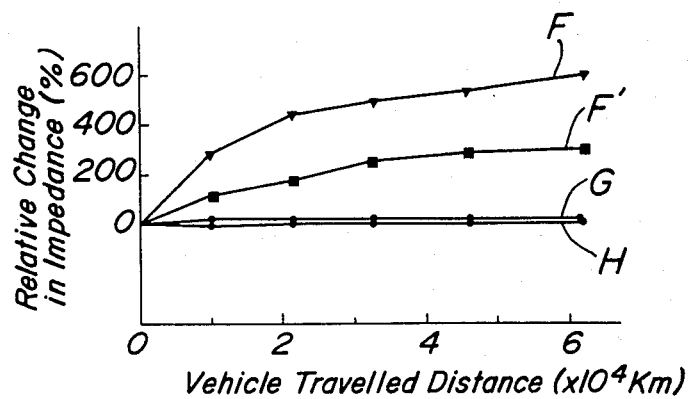
FIG. 7 is a graph showing the relation of the vehicle travelled distance to the variation of the impedance.

The impedance of this oxygen concentration cell varies depending upon the temperature of the solid electrolyte and as the temperature becomes higher, the values of impedance at the points A, B and C become smaller and the frequencies at the points B and C becomes higher. When the impedance corresponding to the temperature variation is measured by applying an AC current having a given frequency to the solid electrolyte, the results as shown in FIG. 6 is obtained and therefore if the impedance is measured, the temperature of the solid electrolyte can be determined. That is, the curve D in FIG. 6 shows the results obtained by effecting the measurement by applying the AC current voltage of the frequency at which the impedance becomes the value of the point B at the temperature $T_2$ and the curve E shows the results obtained by effecting the measurement by applying the AC current voltage of the frequency at which the impedance becomes a value near the point C at the temperature $T_3$. In the present invention, the frequency to measure the impedance is defined to be the frequency at which the polarization of the AC component is caused mainly due to the polarization of the solid electrolyte, that is the frequency within the range from the point B to the point C, preferably the frequency at the point C, because in the case of the curve D in FIG. 6, that is when the temperature is raised from $T_2$ to $T_3$, the impedance varies toward the point A from the point B and within this range, the impedance is highly influenced by the properties of the interface between the electrode and the solid electrolyte and the conditions under which the electrodes are provided and as shown in the curve F in FIG. 7, the impedance is very unstable. This is because in the range between the point A and the point B, the polarization is due to mainly $R_1$ and $C_1$, that is the electrode reaction. FIG. 7 shows the relative variation of impedance at 400° C. in the oxygen concentration sensing device to the vehicle travelled distance and the curve F is the variation (DC) of the impedance corresponding to the point A in FIG. 5, the curve F' is the variation of the impedance corresponding to the frequency at about central point of the arcuate locus extending from the point A to the point B and the curve G and H correspond to the frequencies near the points B and C respectively and the variation of the curves G and H according to the present invention is very small with respect to the use of a long period of time.

In the range of the frequency according to the present invention, that is, at the frequency within the range from the point B to the point C, as far as the variation does not occur in the grain and the grain boundary of the solid electrolyte, $R_2$, $R_3$ and $C_2$ do not vary, so that as shown in the curves G and H in FIG. 7, the impedance is very stable with respect to the use for a long period of time. Stated otherwise, the AC voltage is applied at a frequency which is sufficiently high that the impedance between said electrodes to which AC voltage is applied is largely independent of the interface capacitances between those electrodes and the surface of the solid electrolyte body. Even within the range of the frequency at which the polarization of the AC component is caused mainly due to the polarization of the solid electrolyte, the frequency at the point C, that is the frequency at which the impedance is determined only by the grain of the solid electrolyte, is particularly preferable. Thus the AC voltage is applied at a frequency which is sufficiently high that the impedance between electrodes to which AC voltage is applied is largely independent of the intergrannular capacitance between crystal grains of the solid electrolyte body.

If the Ac voltage for determining the impedance is increased, the solid electrolyte itself can be self-heated and the frequency in this case is preferred to be the frequency in the range between the point B and the point C similarly to the case of measurement of the impedance. This is because within the range from the point A to the point B, the electrode arranging state and the impedance for the use of a long period of time are widely varied and it is difficult to stably apply the electric power necessary for heating and the absolute value of the impedance is about 10 times as high as that from the point B to the point C and unless the value of the AC voltage is increased, it is difficult to supply the electric power and the defects resulting from the increase of the voltage, for example, the conduction trouble from a lead wire, the adverse influence to the electrodes, the cost up of power source and the like are caused. Furthermore, at the frequency in this range a high voltage is applied to the interface between the electrode and the solid electrolyte, so that the peeling off of the electrode and the degradation of the solid electrode are not only caused but also due to a slight difference of the polarizing characteristics between both the electrodes, there might be produced a DC component which is detected in a superimposed manner on the output DC voltage of the oxygen concentration cell, and it is impossible to accurately detect the oxygen concentration.

When the heating of the solid electrolyte is effected by applying the AC voltage of the frequency within the point B to the point C, it does not cause the peeling off of the electrode, the degradation of the solid electrolyte, and the deviation of the direct current component, even if the current is sufficient to heat the solid electrolyte, because when AC voltage having a frequency higher than that at the point B is applied, the most of the polarization is caused in the solid electrolyte equivalent to $R_2$, $C_2$ and $R_3$, and in the interior of the solid electrolyte the polarization is uniformly distributed in a direction of the thickness of the electrolyte, so that the deterioration due to the passing of the current hardly occurs, while the polarization hardly occurs at the interface between the electrode and the solid electrolyte corresponding to $R_1$ and $C_1$ where the deterioration usually occurs, so that the polarization does not effect on the interface. In addition, the impedance within the range from the point B to the point C is dependent upon a characteristic of the solid electrolyte itself without depending upon the attached conditions of the electrodes and variation in quality of the electrodes for a long period of used time, so that when an AC voltage having a frequency within the range B to C is applied, the impedance is low and stable whose value is a fraction or one tenths of the DC resistance with the result that the comparatively low voltage can stably heat the solid electrolyte. In general, the value $R_1$ rapidly increases in comparison with the values $R_2$ and $R_3$ as the temperature lowers, so that the lower limit of the operating temperature of an oxygen concentration detector is limited. In order to eliminate the effect of $R_1$, according to the invention, the AC voltage having a frequency at which the polarization of AC component is caused mainly due to the polarization of the solid electrolyte, or the AC voltage within the range from B to C is applied to flow the current in $R_3$ or $R_2$ and $R_3$ owing to the polarization of the solid electrolyte independent on $R_1$ to heat the electrolyte. Even though the AC frequency to be used for the heating is the frequency due to the polarization of the solid electrolyte, in order to prevent the local heating, the frequency at which the impedance of $C_2$ is smaller than $R_2$, more particularly the frequency at the point C which can effect the heating only by $R_3$ is preferable.

Moreover, the frequencies between the points B and C vary and are not constant depending upon a composition, temperature and shape of the solid electrolyte and shape of the electrodes. In the case of, for example, a bottomed cylinder as shown in FIG. 9 made of a ceramic consisting of 100 parts of a mixture of 95 mol % $ZrO_2$ and 5 mol % $Y_2O_3$ and 3 parts of clay, having an external diameter of 3.5 mm at its bottom end, an effective length 10 mm and a thickness of 0.75 mm and provided on its inner and external surfaces with platinum electrodes, the frequencies at the points B and C are 10 Hz and 50 KHz at 350° C., respectively.

Figure 8:
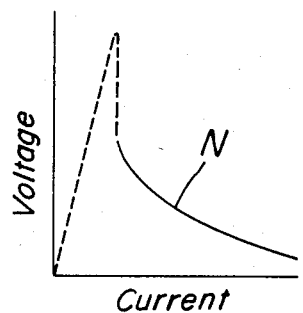
FIG. 8 is a graph showing the voltage-current characteristics when AC is applied to the solid electrolyte.
Figure 17:
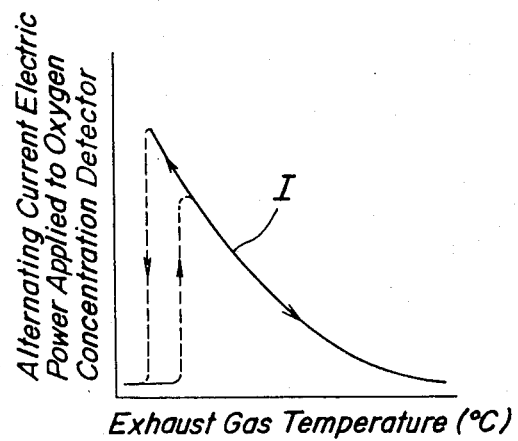
FIG. 17 is a graph showing the relation of the temperature of the oxygen concentration detector to the electric power applied thereto.

FIG. 8 illustrates a relation between electric current and voltage when AC voltage within the range from the point B to the point C is applied to the solid electrolyte, wherein there is a negative relation between the current and voltage, that is one increases, the other decreases, in a zone where the current is more than a determined value (a curve N). This phenomenon is caused by the fact that when an AC current is applied to a resistor to heat it, the resistor itself exhibits a temperature adjusting performance as explained later with FIG. 17. Accordingly, when a resistor is heated, it is preferable to apply the AC current within the zone of the curve N because the AC voltage to be applied becomes lower depending upon the self-heating temperature owing to the above negative relation.

Figure 9:
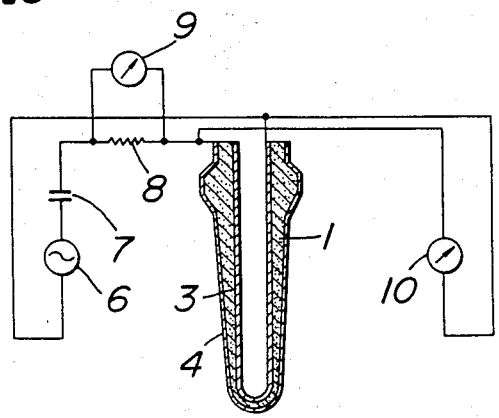
FIG. 9–FIG. 14 are schematic views showing different connecting embodiments of the electrodes of the oxygen concentration cells to be used for the oxygen concentration detector of the present invention.

An explanation will be made with respect to FIG. 9 showing one embodiment of the present invention. An element in which an inner electrode 3 of platinum etc. is provided on an inner surface of a tubular solid electrolyte 1 composed of zirconia ceramics added with yttria and having one closed end and an external electrode 4 is provided on an outer surface of said tubular solid electrolyte and a portion to be contacted with an exhaust gas is covered with a porous protective layer (not shown) in the same manner as in a known oxygen concentration sensing device, is disposed into a gas to be measured, an AC power source 6 having a frequency higher than that of the point B in FIG. 5 is connected to the inner electrode 3 and the external electrode 4 through a direct current component preventing condenser 7 and a current detecting resistor 8 and an AC is passed through the solid electrolyte 1 and the electric current is detected by the current detecting resistor 8 and the AC voltmeter 9 to determine the impedance and concurrently to heat the solid electrolyte, and a DC voltage generated from a concentration cell, located between the inner electrode 3 and the external electrode 4, having the AC simultaneously applied thereto, is detected by a DC voltage sensing device 10.

Figure 10:
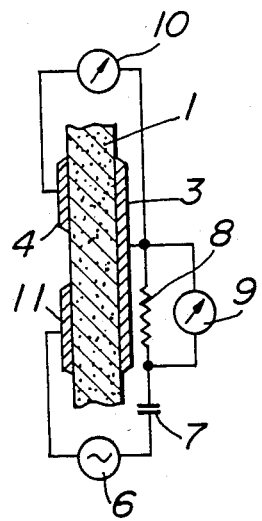
Figure 11:
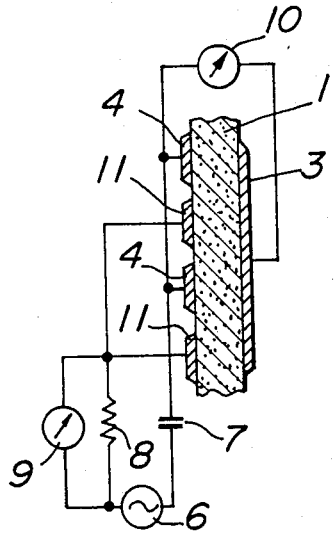
Figure 12:
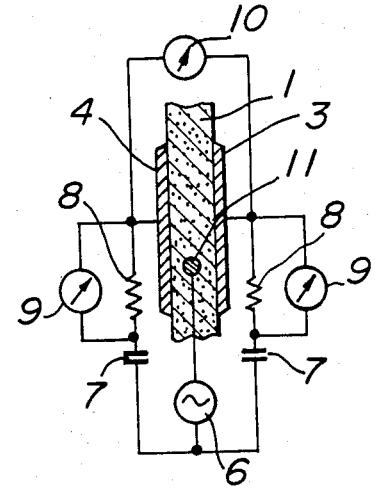
Figure 13:
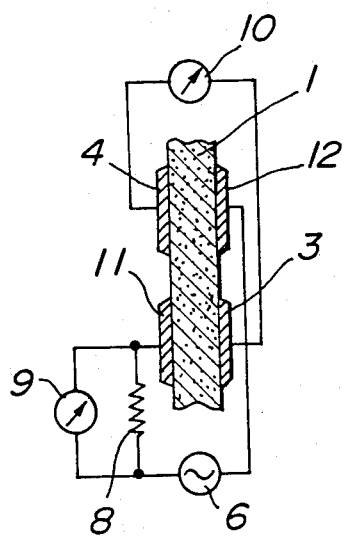
Figure 14:
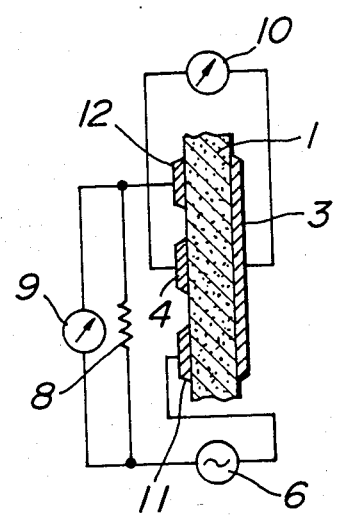

An AC power source for detecting the impedance and an AC power source for heating may be provided separately and may be different in frequency. The electrode to be provided on the solid electrolyte for applying the AC may be used commonly to the inner electrode 3 and the external electrode 4 for the oxygen concentration cell as shown in FIG. 9. Moreover, as shown in FIGS. 10–12, only an AC voltage applying electrode 11 may be independently provided and the other electrode may be commonly used, or as shown in FIGS. 13 and 14, respectively independent AC voltage applying electrodes 11 and 12 may be provided other than the inner electrode 3 and the external electrode 4 of the oxygen concentration cell. Furthermore, AC voltage applying electrodes may be independently provided for detecting the impedance and for heating the electrolyte.

The current detecting resistor 8 for detecting the impedance may be commonly provided with respect to the separated AC voltage applying electrodes 11 as shown in FIG. 11 or may be independently provided respectively as shown in FIG. 12 and if the resistor is independently provided, the temperature at each portion of the solid electrolyte can be separately measured.

In the present invention, if the electrodes for measuring the impedance are commonly used as the electrodes for the oxygen concentration cell or provided in the vicinity of the electrodes for the oxygen concentration cell, the impedance at the portion which controls the electromotive force of the oxygen concentration cell can be detected and the accurate oxygen partial pressure can be determined by using the electromotive force of the oxygen concentration cell and the temperature determined from the impedance. Furthermore, for applying the AC voltage to the oxygen concentration detector and detecting the DC voltage, which is the electromotive force of the oxygen concentration cell, for example, the circuits as shown in FIG. 15 and FIG. 16 can be used.

That is, in FIG. 15, the AC voltage is applied to the oxygen concentration detector 13 from the AC power source 6 through a current stabilizing resistor 14, a current detecting resistor 8 and a condenser 7 for preventing the flowing of DC current while preventing the applying of the DC voltage to the AC source from a condenser 7 for preventing the DC component, to detect the impedance by an AC voltmeter 9 and to heat the solid electrolyte forming the oxygen concentration detector. The DC voltage corresponding to the oxygen concentration from the oxygen concentration detector is detected in the DC voltage detecting device 10 by excluding the AC voltage in the filter circuit composed of a chalk coil 15 and a condenser 16 and the oxygen concentration is measured. The filter circuit is not limited only to one shown in FIG. 15 but other circuit may be used.

The current stabilizing resistor 14 prevents an excess AC from flowing to the oxygen concentration detector 13 and serves to reduce the electric power applying to the oxygen concentration detector 13 at a high temperature at which the heating is not necessary. The relation of the temperature of the exhaust gas to the electric power applied to the oxygen concentration detector is as shown in a curve I in FIG. 17 and at a temperature higher than a certain temperature, if the exhaust gas temperature is raised, the applied electric power is reduced, so that the oxygen concentration detector has a self temperature controlling ability. In FIG. 15 and FIG. 16, the current stabilizing resistor 14 is used but a condenser or a coil may be used instead of the resistor 14 and the current detecting resistor 8 may be a condenser or a coil. Furthermore, the current stabilizing resistor, coil or condenser may be commonly used as the current detecting resistor, coil or condenser and when a condenser is used, said condenser may be commonly used as the DC component preventing condenser 7. The AC voltage may be always applied as in FIG. 15, or the applying of the AC voltage and the detecting of the DC voltage may be alternately changed, or while detecting the impedance, only at a low temperature, the AC electric power is increased to effect the heating and when the temperature is high, the applying of the AC electric power is stopped, or the applied AC electric power is controlled so as to constantly maintain the temperature of the oxygen concentration detector itself.

The solid electrolyte to be used for the oxygen concentration detector of the present invention may be a cylinder form having a closed bottom as shown in FIG. 9 or a plate form or a thin film form as shown in FIG. 10–FIG. 14. In the case of the cylinder having the closed bottom, the form as shown in FIG. 9 wherein the thickness at the top portion is the most thin, is best because the local heat can be stably generated. This is because the electric resistance per unit surface area at the top end portion becomes smallest, so that when the AC voltage is applied, the electric current concentrates at this top portion and the top portion is selectively heated. Accordingly, the electric power necessary for heating may be an amount balancing the dissipated heat at the top end portion and the top end portion of the solid electrolyte is heated by supplying a very slight amount of AC electric power and the oxygen concentration detector has a rapid response and a low impedance even at a relatively low temperature of ambient atmosphere. In this manner, the portion to be heat generated may be thinner in the thickness than the other portions and as shown in FIG. 10–FIG. 14, the heat generating portion may be selected by providing the electrodes at such portions and the responsibility is more improved by selecting the heat generating portion at the portion where the contact with the gas to be measured is most easy. The portion for detecting the impedance may be selected by the portion where the electrodes are provided. Even when the local heating is effected, if the process of the present invention in which the temperature of the solid electrolyte is measured by detecting the impedance, is adopted, the impedance when the solid electrolyte is operated, can be measured, so that even in the local heat generation, the temperature of the solid electrolyte can be precisely and accurately determined. Since the solid electrolyte to be heated is negative in the temperature characteristics of the solid electrolyte, the resistance value at a low temperature is high and there is a case where an enough current to heat the solid electrolyte can not be passed, and in such a case, it is preferable that an auxiliary heater is embedded in the solid electrolyte or disposed in the vicinity of the resistor to preheat electrolyte to the temperature at which a sufficient current passes through the solid electrolyte.

The following example is given for the purpose of illustration of this invention and is not intended as limitations thereof.

An oxygen concentration detector was prepared by providing an inner electrode 3 and an external electrode 4 respectively on an inner surface and an outer surface of a cylindrical solid electrolyte having a closed end bottom as shown in FIG. 9 and composed of zirconia ceramics prepared by adding 3 parts of clay to 100 parts of a mixture of 95 mol% of $ZrO_2$ and 5 mol% of $Y_2O_3$, wherein the top end portion has an outer diameter of 3.5 mm and an inner diameter of 2 mm and the central portion has an outer diameter of 5 mm and an inner diameter of 2.5 mm and adhering a spinel porous layer on the surface of the external electrode 4. This detector was disposed in an engine exhaust gas of an already known air fuel ratio $\lambda_1$ shown in Table 1 and the air-fuel ratio $\lambda_1$ was gradually varied and the temperature of the solid electrolyte was determined from the impedance measured by the electromotive force of the oxygen concentration detector and a sine wave of a frequency of 50 KHz and a voltage of 10 mV, and the air-fuel ratio $\lambda_2$ was determined from the temperature and the electromotive force. The measured results are shown in Table 1.

TABLE 1

| Exhaust gas temperature | $\lambda_1$ | $\lambda_2$ |
|---|---|---|
| about 350° C. | 0.90 | 0.91 |
| | 1.00 | 1.00 |
| | 1.10 | 1.11 |
| about 850° C. | 0.90 | 0.89 |
| | 1.00 | 1.00 |
| | 1.10 | 1.10 |

As seen from the Table 1, the already known air-fuel excess ratio $\lambda_1$ and the measured air-fuel excess ratio $\lambda_2$ showed substantially equal values. This measurement was carried out with respect to both cases of the exhaust gas temperature of about 350° C. and about 850° C.

Then, the voltage of the AC voltage was raised to 70 V and about 2 W of electric power was applied to the solid electrolyte by using a current stabilizing resistor and the above described exhaust gas temperature was set at about 250° C. and the time necessary for varying the electromotive force of the oxygen concentration sensing device from 0.6 V to 0.3 V or from 0.3 V to 0.6 V when the air-fuel ratio was varied from $\lambda=0.9$ to $\lambda=1.0$ and when said ratio was varied from $\lambda=1.1$ to $\lambda=0.9$, and the temperature of the oxygen concentration detector obtained by the measurement of the impedance were determined. The obtained results are shown in Table 2.

TABLE 2

| | Present invention | | Prior art | |
|---|---|---|---|---|
| Exhaust gas condition | Response (sec) | Element temperature (°C.) | Response (sec) | Element temperature (°C.) |
| R–L | 0.05 | | 0.97 | |
| | | 473 | | 242 |
| L–R | 0.02 | | 0.19 | |

R–L: Variation from $\lambda = 0.9$ to $\lambda = 1.1$
L–R: Variation from $\lambda = 1.1$ to $\lambda = 0.9$
Response: Time necessary for variation of the electromotive force of 0.6 V ←→ 0.3 V.

In the oxygen concentration detector of the present invention, the temperature of about 230° C. was raised by an electric power of only 2 W and the very good responsibility was shown with respect to the variation of the gas to be measured but in the case of the prior embodiment wherein the electrodes are not heated, the responsibility at a low temperature was very poor. When the measurement of the impedance and the heating were concurrently conducted by gradually varying the air-fuel ratio in the same manner as described above, substantially the same values as in Table 2 were obtained.

Figure 18:
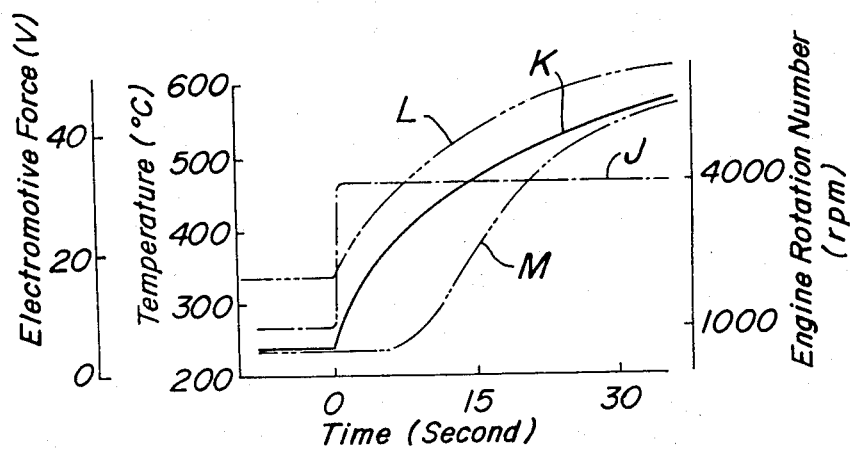
FIG. 18 is a diagram showing the measured results of the example of the present invention.

The temperature variation of the solid electrolyte was determined by the variation of the exhaust gas temperature, the variation of the electromotive force of the oxygen concentration sensing device and the variation of the impedance when the air-fuel ratio in the engine exhaust gas system was permitted to be approximately 1.1 and the rotation number of engine was raised rapidly from 1,000 r.p.m. to 4,000 r.p.m. For comparison, the temperature variation of the solid electrolyte was measured by means of the temperature detecting element with respect to the prior oxygen concentration detector wherein a temperature detecting element is inserted into the cylinder as shown in FIG. 1. The results are shown in FIG. 18. When the engine rotation number (curve J) was varied from 1,000 r.p.m. to 4,000 r.p.m., the temperature of the solid electrolyte determined from the impedance of the oxygen concentration detector of the present invention is shown in a curve K and is quite similar to a curve L showing the variation of the electromotive force and rapidly follows to the variation of the exhaust gas temperature. While, the prior embodiment as shown in FIG. 1 is shown in a curve M in which the temperature is fairly slowly detected as compared with the curve L showing the variation of the electromotive force and therefore the temperature correction of the electromotive force when the exhaust gas temperature is varied, is delayed and the determination of the oxygen concentration is not accurate.

As mentioned above, the oxygen concentration detector of the present invention can measure accurately and stably the substantial temperature of the solid electrolyte for a long period of time only by means of the oxygen concentration detector without using a separate temperature detecting element, so that the oxygen concentration can be accurately measured and the air-fuel ratio λ of the internal combustion engine can be controlled at an optical value other than 1.0 and further by self-heating the solid electrolyte through passing an AC current, the measurement can be effected at a low impedance in a high responsibility even by a low temperature gas and further the temperature detecting portion and the heating portion can be optionally selected and by detecting the temperature to control the heating electric power, the solid electrolyte itself can be maintained at a given temperature. Accordingly, the oxygen concentration detector of the present invention can be utilized particularly for measuring the oxygen concentration in the exhaust gas discharged from the internal combustion engines and is commercially very useful.

What is claimed is:

1. An oxygen concentration detector for detecting the oxygen concentration in gases comprising:
   an oxygen ion conductive solid electrolyte body;
   a plurality of separate electrodes contacting the solid electrolyte body, at least two of said plurality of separate electrodes having the solid electrolyte body therebetween, thereby forming an oxygen concentration cell for detecting oxygen partial pressure in a gas;
   electromotive force detecting means connected to at least two of said plurality of separate electrodes having the solid electrolyte body therebetween, for detecting an electromotive force of the oxygen concentration cell;
   AC supply means connected to at least two of said plurality of separate electrodes having the solid electrolyte body therebetween, for applying an AC voltage to said solid electrolyte body through said electrodes, said AC supply means being arranged to supply an AC voltage at a frequency sufficiently high such that an impedance between said electrodes to which AC voltage is applied is largely independent of interface capacitances between said electrodes to which AC voltage is applied and a surface where said separate electrodes contact said solid electrolyte body; and
   impedance detecting means connected to at least two of said plurality of separate electrodes having the solid electrolyte body therebetween, for detecting an impedance of said solid electrolyte body.

2. An oxygen concentration detector for detecting the oxygen concentration in gases comprising:
   an oxygen ion conductive solid electrolyte body;
   a plurality of separate electrodes contacting the solid electrolyte body, at least two of said plurality of separate electrodes having the solid electrolyte body therebetween, thereby forming an oxygen concentration cell for detecting oxygen partial pressure in a gas;
   electromotive force detecting means connected to at least two of said plurality of separate electrodes having the solid electrolyte body therebetween, for detecting an electromotive force of the oxygen concentration cell;
   at least one other electrode contacting the solid electrolyte body;
   AC supply means connected to said at least one other electrode and at least one of said plurality of separate electrodes, said at least one other electrode and said one of said plurality of separate electrodes having the solid electrolyte body therebetween, for applying an AC voltage to said solid electrolyte, said AC supply means being arranged to supply an AC voltage at a frequency sufficiently high that an impedance between said electrodes to which AC voltage is applied is largely independent of interface capacitances between said electrode to which AC voltage is applied and a surface where said one other electrode and said one of said plurality of separate electrodes contact said solid electrolyte body; and
   impedance detecting means connected to said other electrode and one of said plurality of separate electrodes, having the solid electrolyte body therebetween, for detecting an impedance of said solid electrolyte.

3. The detector of claim 1 or 2, wherein the AC has a frequency which is sufficiently high that the impedance between said electrodes to which AC voltage is applied is largely independent of an intergranular capacitance between crystal grains of said solid electrolyte body.

4. The detector of claim 1, wherein said supplied AC voltage causes the solid electrolyte body to be self-heated.

5. The detector of claim 4, wherein said at least two of said plurality of separate electrodes for the electromotive force detecting means are the same electrodes as said at least two of said plurality of separate electrodes for the impedance detecting means.

6. The detector of claim 4, wherein at least one of said at least two of said plurality of separate electrodes for the electromotive force detecting means is the same electrode of at least one of said at least two of said plurality of separate electrodes for the impedance detecting means.

7. The detector of claim 2, wherein said supplied AC voltage causes the solid electrolyte body to be self-heated.

8. The detector of claim 4 or 7, wherein the AC current and the AC voltage between the electrodes have a negative relation, in which when one increases, the other decreases.

9. The detector of claim 4 or 7, wherein the AC has a frequency which is sufficiently high that the impedance between said electrodes to which AC voltage is applied is largely independent of intergranular capacitances between crystal grains of said solid electrolyte body.

10. The detector of claim 1, wherein said at least two of said plurality of separate electrodes for the electromotive force detecting means are the same electrodes as said at least two of said plurality of separate electrodes for the impedance detecting means.

11. The detector of claim 1, wherein at least one of said at least two of said plurality of separate electrodes for the electromotive force detecting means is the same electrode of at least one of said at least two of said plurality of separate electrodes for the impedance detecting means.

* * * * *